(12) United States Patent
Wang

(10) Patent No.: US 8,406,856 B2
(45) Date of Patent: Mar. 26, 2013

(54) OPTICALLY CHARACTERIZING TURBID MEDIA AND SUBSTANCES IN TURBID MEDIA

(75) Inventor: Feiling Wang, Medford, MA (US)

(73) Assignee: Alethus, Inc., Medford, MA (US)

( * ) Notice: Subject to any disclaimer, the term of this patent is extended or adjusted under 35 U.S.C. 154(b) by 90 days.

(21) Appl. No.: 13/139,479

(22) PCT Filed: Jun. 20, 2009

(86) PCT No.: PCT/US2009/003698
§ 371 (c)(1),
(2), (4) Date: Jun. 13, 2011

(87) PCT Pub. No.: WO2009/154798
PCT Pub. Date: Dec. 23, 2009

(65) Prior Publication Data
US 2011/0245686 A1  Oct. 6, 2011

Related U.S. Application Data

(60) Provisional application No. 61/132,546, filed on Jun. 20, 2008, provisional application No. 61/191,972, filed on Sep. 15, 2008.

(51) Int. Cl.
*A61B 6/00* (2006.01)
(52) U.S. Cl. .......................................... 600/473; 600/476
(58) Field of Classification Search .................. 600/473, 600/476
See application file for complete search history.

(56) References Cited

U.S. PATENT DOCUMENTS

| 2003/0218756 A1 | 11/2003 | Chen et al. |
| 2004/0228005 A1 | 11/2004 | Dowski |
| 2006/0180750 A1 | 8/2006 | Gollier et al. |
| 2006/0182382 A1 | 8/2006 | Gollier et al. |

FOREIGN PATENT DOCUMENTS

JP   2005017104 A   1/2005

OTHER PUBLICATIONS

International Search Report and Written Opinion dated Feb. 2, 2010 for International Application No. PCT/US2009/003698, filed Jun. 20, 2009 (6 pages).
International Preliminary Report on Patentability dated Dec. 21, 2010 for International Application No. PCT/US2009/003698, filed Jun. 20, 2009 (4 pages).
Wang, F. "Binary phase masking for optical interrogation of matters in turbid media," Optics Letters, 33 (22):2587-2589, 2008.

*Primary Examiner* — Peter Luong
(74) *Attorney, Agent, or Firm* — Perkins Coie LLP

(57) ABSTRACT

For optically interrogating substances overlaid by turbid media a method of wavefront manipulation by means of binary phase masking is disclosed. Through altering the degree of mode conformity between the fields reaching the collection optics and the field distributions of the propagation modes of optical waveguides the disclosed method can be used to suppress the collection of short-range light originated near the collection optics while permitting unimpeded collection of light originated from sites substantially behind turbid media.

19 Claims, 15 Drawing Sheets

OPTICALLY CHARACTERIZING TURBID MEDIA AND SUBSTANCES IN TURBID MEDIA

PRIORITY CLAIMS

This application claims the priority of U.S. Provisional Application No. 61/132,546 entitled "Optical measurement of subsurface analyte" filed on Jun. 20, 2008" and U.S. Provisional Application No. 61/191,972 entitled "Optically characterizing matters in turbid media" filed on Sep. 15, 2008.

BACKGROUND

Non-invasive or in vivo interrogation of biological tissues with light waves is becoming increasingly important in medicine. Some of the techniques employed are diffuse-reflectance spectroscopy, fluorescence spectroscopy, imaging etc. In many of these cases, the targeted tissues are subsurface. For example, in non-invasive monitoring of blood glucose with reflectance spectroscopy, the targeted issue is the subsurface dermis where glucose-retaining vasculature and interstitial fluids reside. However, a substantial portion of the collected light originates from the superficial epidermis layer which not only yields no useful information but also interferes with the characterization of the dermis tissue. It is particularly obstructive because the optical properties of the epidermis is highly affected by pigmentation, hydration and temperature variation, all of which prevents an accurate determination of the blood glucose even with elaborated calibration schemes.

The disclosed in this application includes a method and its embodiments for the characterization of subsurface tissues by suppressing the collection of light from the superficial layer that the probing light encounters. The invented method and techniques can benefit a variety of optical characterization procedures in which the targeted tissue is subsurface, as in the case of non-invasive monitoring of blood glucose. Also disclosed in this application is a method of acquiring cross-sectional tissue images of biological tissues and other matters with improved imaging depth and clarity.

DESCRIPTION

Figure 1:
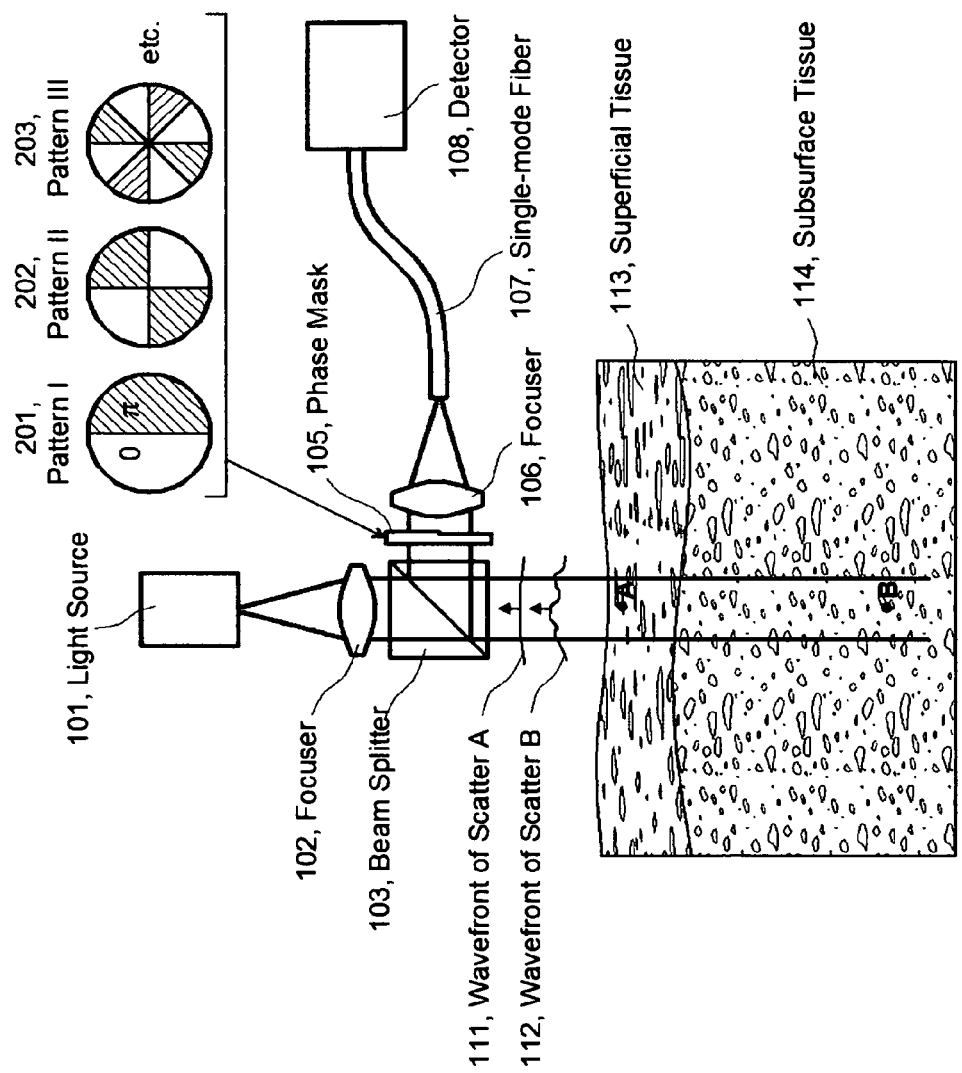
FIG. 1 shows an optical arrangement in which a binary phase mask is inserted in the path of the backscattered light by the tissue under examination.

Living tissues can be considered as turbid media in which light experiences absorption and scattering. For assays and related processes light beams can be sent into tissues of interest; the backscattered light can be collected for analyses. In such a process, the collected light includes contributions from the specular reflection of the surface, backscattering of the superficial tissue layer and backscattering of the subsurface tissue. For skin, the epidermis and dermis can be considered superficial layer and subsurface tissue, respectively. The specular reflection produces the least amount of wavefront distortion; the backscattered light from the superficial layer can carry substantial wavefront distortion as multiple scattering is involved; the most severe wavefront distortion is associated with light originated from scatters in the subsurface tissue.

Single-mode optical fibers can be conveniently used for delivering light to the tissue of interest and collecting backscattered light from the tissue. A property of single-mode optical fibers is that it permits only one propagation mode of light, namely, the fundamental mode. When a single-mode fiber is used for collecting light, it accepts only light waves with spatial amplitude and phase distributions that conform to those of the fundamental mode. Specifically, the fundamental mode requires the incoming light wave to have a Gaussian distribution. If the incoming light deviates from Gaussian only the portion of the light that conforms to it will be collected and propagate in the fiber. Mathematically, we speak of the mode conformity of the incoming light wave with the fundamental propagation mode of the fiber in terms of the following mode-conformity integration (for simplicity, a collimated Gaussian beam with spot size w, determined by the numerical aperture of the fiber and the focusing optics, is assumed):

$$\left| \int\int_A e^{-\frac{r^2}{w^2}} \cdot \tilde{E}(x,y) \cdot dA \right|^2, \qquad (1)$$

where $\tilde{E}(x,y)$ is the electric field of the backscattered light. If $\tilde{E}(x,y)$ is a conforming Gaussian this integral yields a maximum—all the optical energy will be collected and propagate in the fiber. There can be situations in which the mode-conformity integral is zero—no optical energy will be collected or allowed to propagate in the fiber. An example for a zero conformity is when the returning electric field has the following form:

$$\tilde{E}(x, y) = \begin{cases} E_o e^{-\frac{r^2}{w^2}}, & x < 0 \\ -E_o e^{-\frac{r^2}{w^2}}, & x \geq 0, \end{cases} \quad (2)$$

which is a Gaussian beam except that electric field changes sign crossing from the left half to the right half of the beam. This field distribution can be created by inserting a binary phase mask that has an optical phase step of $\pi$ in the middle of a Gaussian beam.

Although for many commercially available optical fibers the fundamental propagation modes can be approximated by Gaussian distribution, it should be appreciated that optical fibers can have fundamental propagation modes with field distribution, $E_m(x,y)$, which is non-Gaussian. In this case the mode-conformity integral takes the following, more general form:

$$\left| \int\int_A E_m(x, y) \cdot \tilde{E}(x, y) \cdot dA \right|^2, \quad (3)$$

The above-mentioned conditions for launching a propagating beam in a single-mode fiber can be utilized for suppressing the collection of the backscattered light originated from the superficial tissue while permitting the collection of light backscattered from subsurface tissues. The optical arrangement shown in FIG. 1 is an exemplary realization. In this setup, the collection optics consists of Phase Mask 105, Focuser 106, Single-mode Fiber 107 and Detector 108. Phase Mask 105 is binary: it has two phase values, 0 and $\pi$, with many possible geometric distributions as 201, 202 and so on, all of which have zero mode conformity with the fundamental mode of the single-mode fiber. Now for backscattered light originated from the superficial layer with negligible wavefront distortion (phase aberration) the phase mask destroys its conformity with the fundamental propagation mode of the fiber, therefore the light cannot propagate to reach the detector. For backscattered light originated from a subsurface region with severe wavefront distortion, a substantial mode conformity can exist with the fundamental propagation mode of the single-mode fiber after passing through the phase mask, therefore a substantial optical power can reach the detector. For light waves originated from deep scatters, such as Scatter B, the wavefront distortion is so severe and randomized that, statistically, its conformity with the fundamental propagation mode of the fiber is not affected by the presence of the phase mask. The optical arrangement of FIG. 1 can then suppress photons from the superficial layer and, on a statistical average basis, provides a gradually increasing passage to photons originated from a gradually increasing depth from the surface.

Many other geometric patterns can be adopted for the binary phase mask. The several shown in FIG. 2, except Pattern 200, all have zero conformity with the fundamental propagation mode of the fiber, and with one another including Pattern 200 which is no phase aberration at all. The mutual orthogonality of the phase patterns means that photons being collected after passing through one of the phase patterns will be rejected by the fiber if another phase pattern is used. For the purpose of blocking photons associated with undistorted wavefront (originated from the superficial layer), any of the phase patterns, except 200, can be used.

The choice of phase pattern should be based on many considerations, including knowledge of the wavefront characteristics, the desired effects, the specific optical design adopted and the manufacturability. In general, phase pattern of a certain spatial frequency tends to block photons associated with wavefronts randomized at lower spatial frequencies. This means that more complex phase patterns have stronger blocking power compared to simpler ones. The wavefront characteristics of the targeted tissues are not generally known. In these cases, it may be desirable and preferable to carry out experiments in order to determine which phase pattern is optimal for the desired effect.

Alternative to using a fix phase mask, a system can be designed to cycle through two or more applicable phase patterns. The cycling can be accomplished by either mechanically exchanging the phase masks or by controlling an electro-optic plate, or by controlling a device based on micro-electro-mechanical system (MEMS).

An advantage of cycling through a series of orthogonal phase patterns is that the photocurrents measured with different phase patterns can be summed up to have an integrated photocurrent which is less dependent on the specific wavefront, therefore, less dependent on the local distribution of the scatters. In other words, the integrated photocurrent is more stable and less site specific, which can facilitate more accurate characterization of the subsurface tissue.

Figure 3:
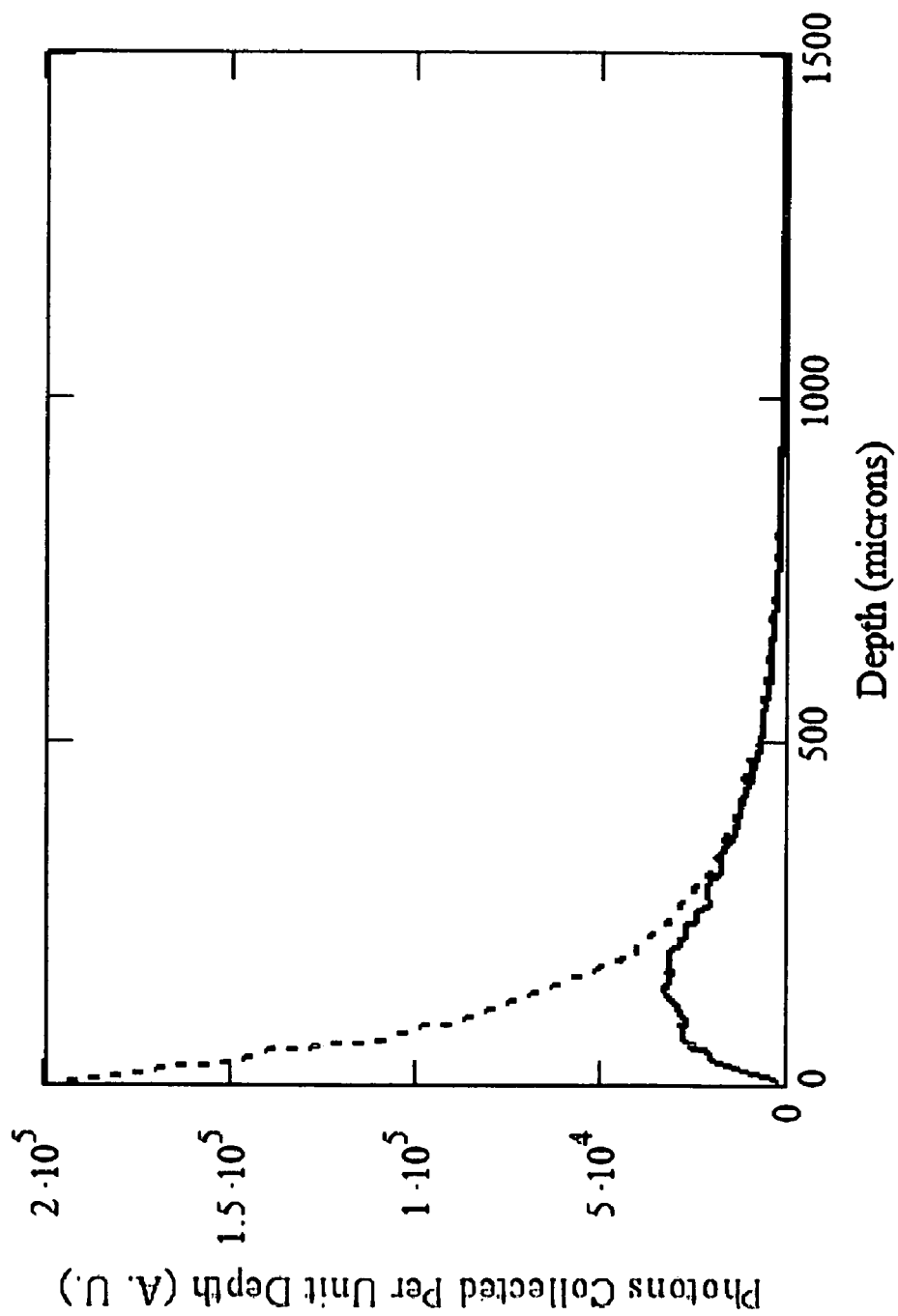
FIG. 3 shows the collection of light from the tissue under examination as a function of depth with and without the insertion of a binary phase mask. The dashed curve shows the situation without the mask; the solid curves shows the situation with a binary phase mask.

Shown in FIG. 3 are the results of a computer simulation of light collection using the optical system shown in FIG. 1, with and without phase mask of pattern 201. The dashed line is the collected photons per unit depth (4 microns) without the phase mask, as in the conventional technology, as a function of the depth. It follows an exponential function of the depth due to the attenuation of the light beam in the turbid medium (tissue); a vast majority of the collected photons originate from the superficial layer (within the first 200 micron or so). When the phase mask is in place, the photons originated from the superficial layer are substantially rejected by the single-mode fiber, as shown by the solid line. The effect of the phase mask gradually diminishes for photons originated from increasingly greater depths because they carry increasingly more severe wavefront distortions. For photons originated beyond the depth of 300 microns, they are equally likely collected by the single-mode fiber with or without the phase mask, shown by the coincidence of the solid and the dashed lines beyond the depth of 300 microns.

If an optical system similar to what shown in FIG. 1 is used for monitoring blood glucose concentration it can drastically increase the ratio of photons originated from the dermis to that originated from the epidermis in the overall collected light. The high ratio promotes more accurate determination of the glucose concentration. If photons are collected in the two states, i.e. with and without the phase mask, from the same sampling site, more detailed and layer-specific tissue characteristics can be deduced.

Figure 4:
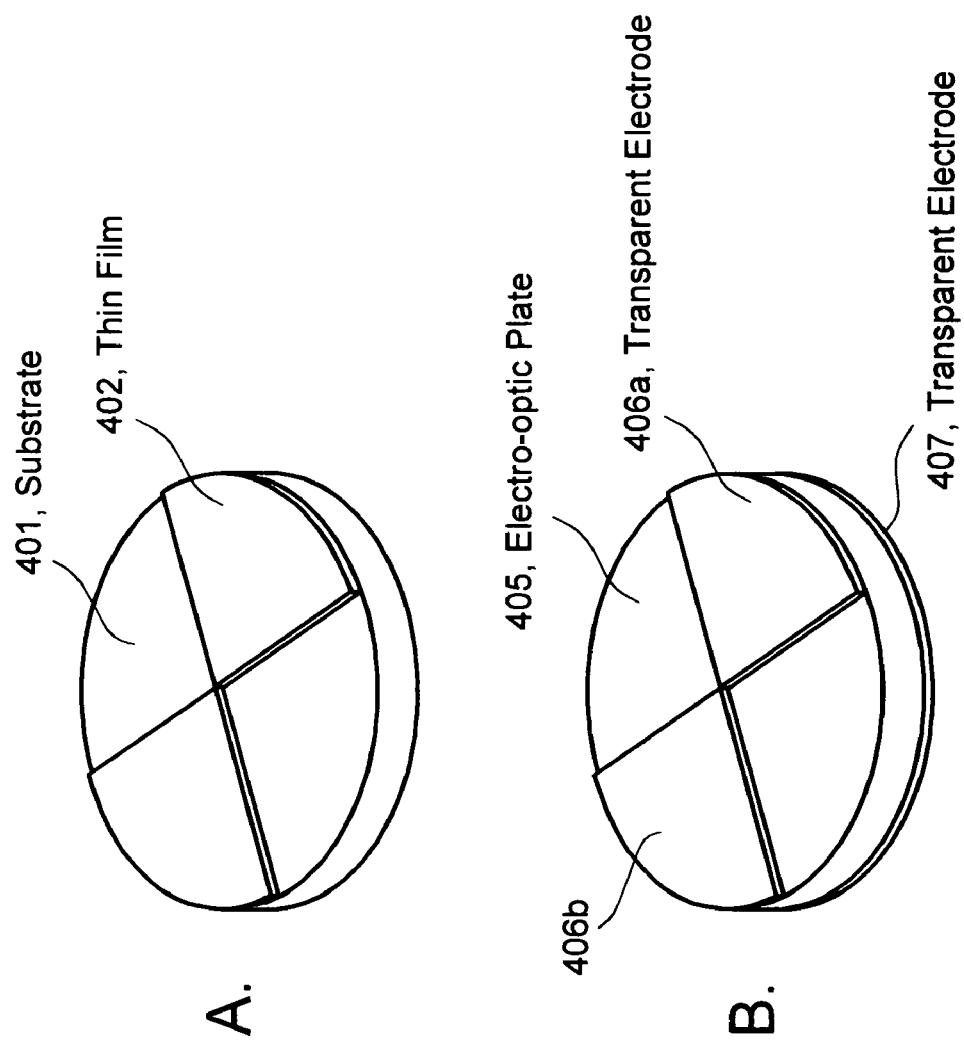
FIG. 4 shows two of the possible ways of constructing binary phase masks.

Phase masks can be either static or dynamic. Conventional optics manufacturing methods can be employed for the fabrication of these phase masks. Static masks can be fabricated on transparent substrates, such as glass or quartz. Shown in FIG. 4(A) is one of the many possible constructions of Pattern 201. A layer of thin film optical material, 402, can be deposited on two of the four quadrants of the substrates. The substrate surfaces should be sufficiently flat and parallel to one another. In a preferable embodiment, the thickness D of the thin film material is determined by the following equation:

$$D = \frac{\lambda}{2 \cdot (n-1)}, \quad (4)$$

where n is the refractive index of the thin film material; λ is the center wavelength of the light source. The thin-film material can be chosen to have a refractive index similar to that of the substrate. Dynamic phase masks can be manufactured with an electro-optic substrate. Possible electro-optical materials for the purpose include, but not limited to, single-crystal materials as lithium niobate, polycrystalline materials (ceramics) as lead lanthanum zirconate titanate, as well as liquid crystal materials. One of the possible construction of a dynamic phase mask with pattern 201 is shown in FIG. 4(B). A solid electro-optic material is used as the substrate. One side of the electro-optic plate is entirely coated with a transparent and conducting thin film material such as indium-tin oxide (ITO) to be Electrode 407; two opposite quadrants of the other surface are coated with the thin film material to be Electrode 406. The thickness of the transparent and conducting thin film can be chosen to be an integer multiple of the light wavelength. When an appropriate electric field is applied to the electro-optic material through Electrode 406 and Electrode 407 the two electroded quadrants can have an optical thickness that is one half of the light wavelength in reference to the unelectroded quadrants.

By applying and withdrawing the electric field across the electro-optic material one can measure the backscattered light in two states: with and without suppression of the photons from the superficial layer. Computations with these two signals allows extraction of the optical properties of the superficial and the subsurface tissues, respectively. If a broadband light source is used and a spectral analysis is applied to the two signals it is possible to separate the spectral characteristics of the superficial layer and the subsurface tissue. This can greatly benefit the accurate determination of subsurface analyte such as blood glucose.

Figure 2:
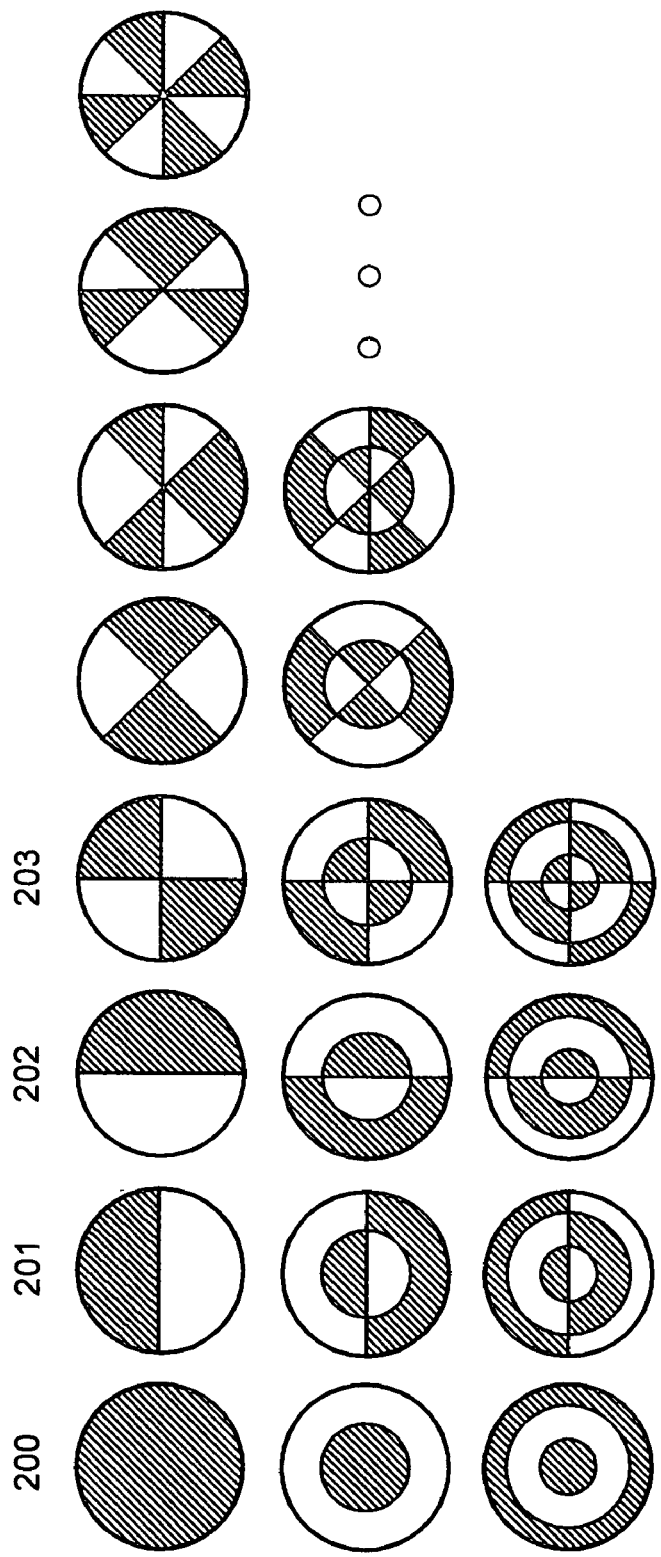
FIG. 2 shows a group of phase patterns which can be used to form the binary phase mask. The shades areas and clear areas have different optical path length; when the difference is half of the optical wavelength all these patterns are mathematically orthogonal.

With an electro-optic material a plurality of phase patterns, such as all that are shown in FIG. 2, can be generated in one device. They can be realized by selectively applying electric field to segmented electrodes.

Figure 5:
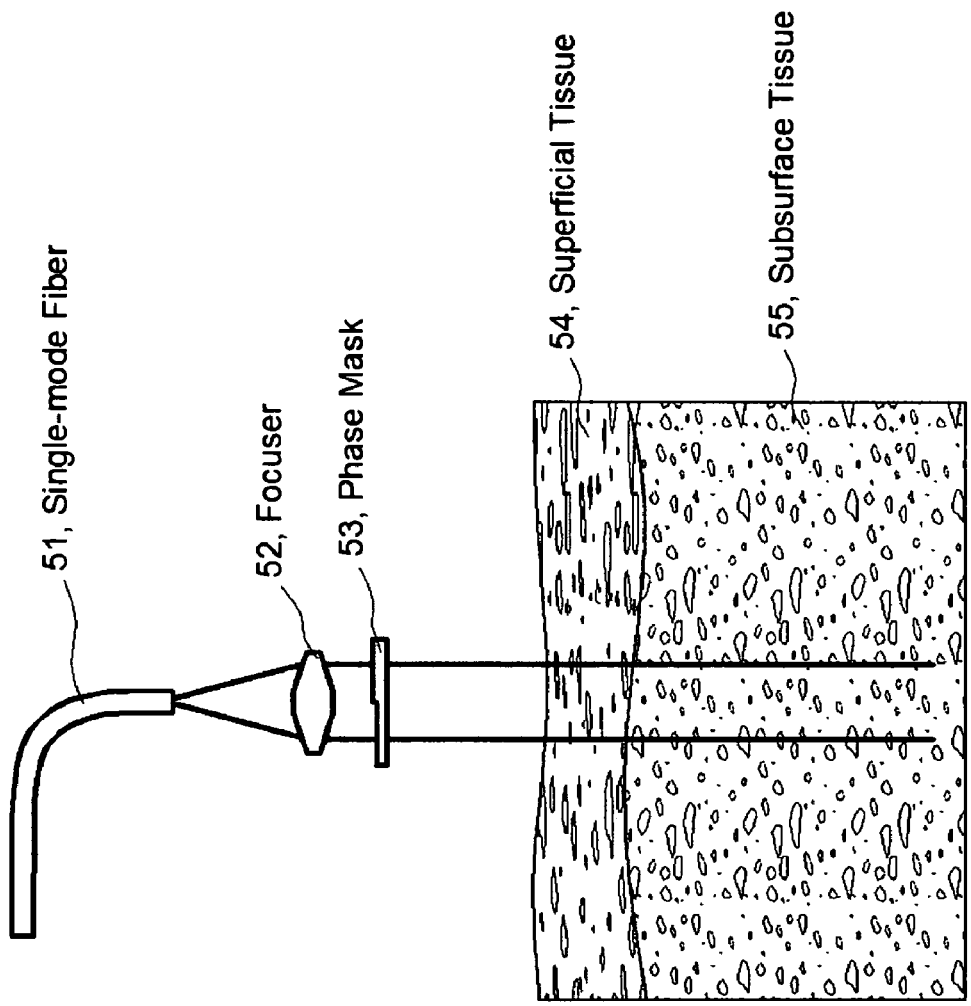
FIG. 5 shows an optical arrangement in which a single-mode optical fiber is used for both delivering to and collecting light from the tissue.
Figure 6:
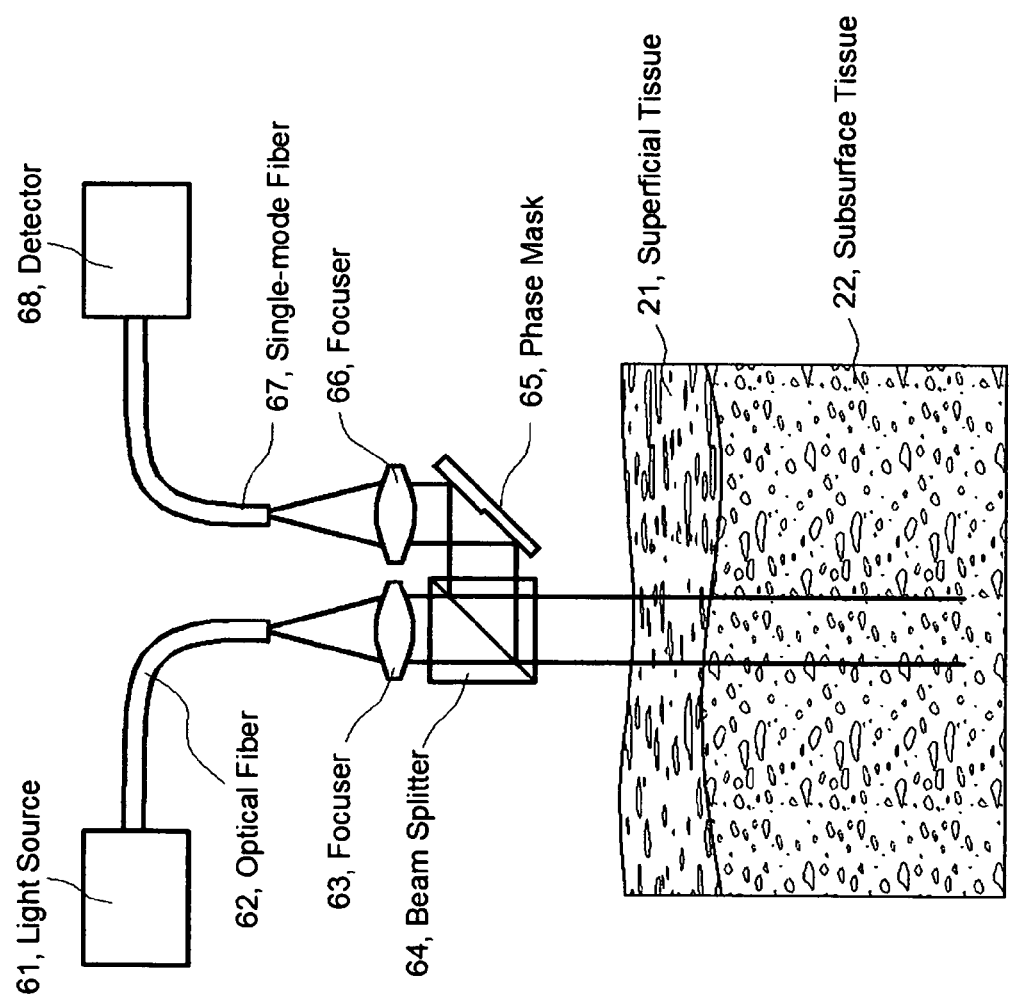
FIG. 6 shows an optical arrangement in which a reflection-mode binary phase mask is used in the path of the light collected from the tissue backscattering.

Many other optical arrangements are possible for the embodiment of the invention. Shown in FIG. 5 is a system in which one single-mode fiber is used for both delivering light to and collecting light from the tissue. A reflective phase mask can also be used in an optical arrangement shown in FIG. 6. Phase Mask 65 can be either static or adjustable. Mechanism for the adjustable phase masks can be electro-optic, magneto-optic or micro-mechanic.

Figure 7:
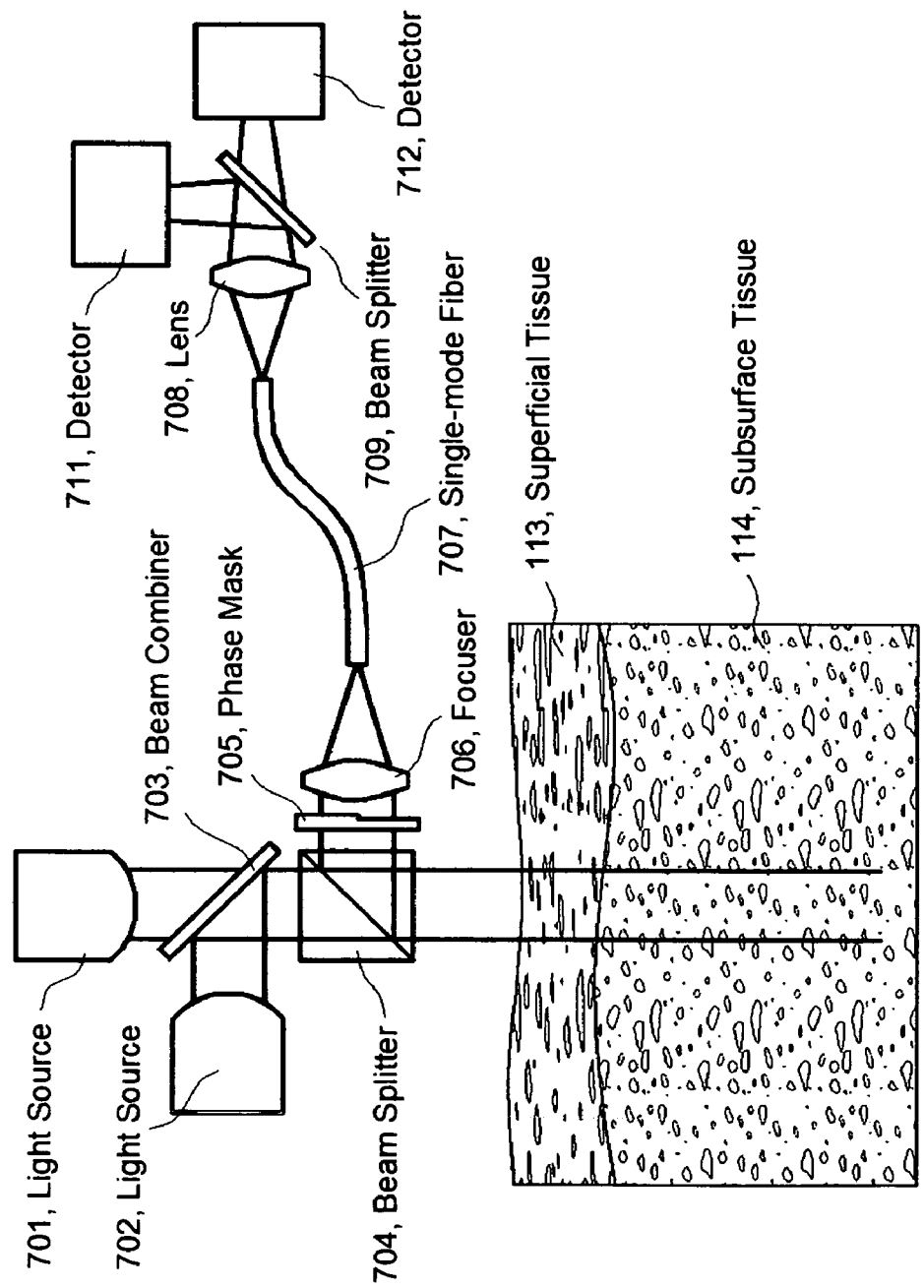
FIG. 7 shows an optical arrangement in which a plurality of light sources are used.

It is often desirable to compare the absorption and scattering properties of tissue at different wavelengths. In some case a single light source, either a broadband light source such as a superluminescent light emitting diode (SLED) or tunable source such as a tunable laser, can cover the spectral range of interest. In other cases, it is more convenient to bring together light beams from multiple light sources, each covering a different wavelength band. The optical arrangement shown in FIG. 7 is one of the possible ways of accomplishing that. In this arrangement, one phase mask is and one single-mode fiber are used for the backscattered light at different wavelengths. Two dichroic beam splitters, 703 and 709, are used to combine and separate light beams in different wavelength bands. The two photodetectors receive the collected light in the different wavelength bands, respectively. Comparisons of the two detected signals can lead to more accurate determination of certain analyte that has a characteristic absorption at one wavelength. The second wavelength can be used for calibration.

In certain applications it is desirable to study detailed spectroscopic characteristics of the backscattered light. For that purpose, a spectrometer can be used with a broadband light source. For instance, Detector 108 in FIG. 1 can be a spectrometer to analyze the spectrum provided by Light Source 101. Alternatively, a single element photodetector can be used with a tunable laser in the same optical arrangement.

Figure 8:
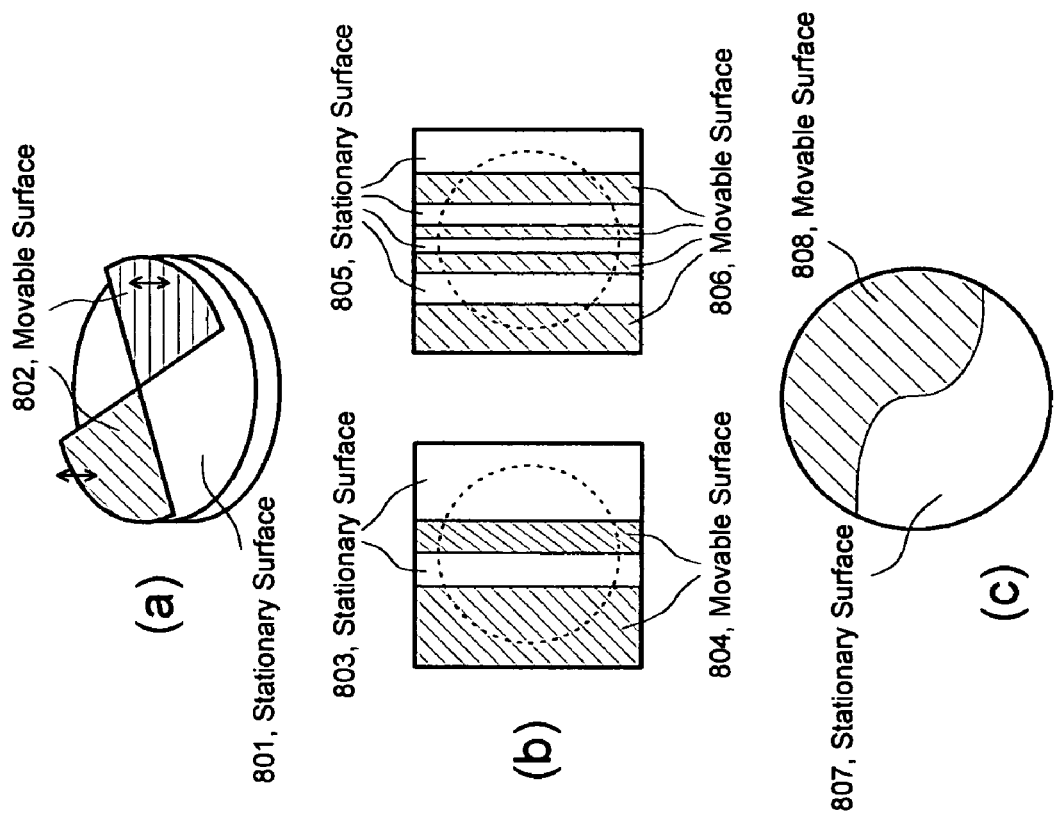
FIG. 8 shows some of the possible ways of segmenting and constructing the binary phase masks.

In addition to what described earlier, reflection-mode and tunable binary phase masks can be designed and manufactured using the micro-electro-mechanical system (MEMS) technology. Shown in FIG. 8 are possible designs for MEMS based reflective phase masks. FIG. 8(A) is a design with the same phase pattern as example in FIG. 4; two of the quadrants have stationary reflection surface and the remaining two quadrants have movable reflection surface, actuated through an electric signal.

For ease of fabrication, strip phase patterns, such as what shown in FIG. 8(B), may be used. The widths of the strips should be designed to make sure that the stationary strips and movable strips have the same integral value with the mode field so that the total mode-conformity integral, Eq. (1) or (3), is zero when a π phase shift is generated by moving the movable strips. These strip phase patterns can also be adopted for static binary phase masks and electro-optically tunable phase masks of transmission mode. Binary phase masks can also adopt irregular phase patterns, such as the one shown in FIG. 8(C).

When the light sources is monochromatic or narrow band, a static phase mask may be suitable and can be made with simple method such as depositing and patterning a layer of thin film material. If broad band light sources are used, achromatic phase masks may be necessary. Achromatic phase mask can be manufactured with the same manufacturing method as achromatic wave plates, commercially available. If broad-band tunable light sources are used, dynamic phase make will have advantageous as the condition of π phase retardation can be strictly tracked through controlling the mask.

Figure 9:
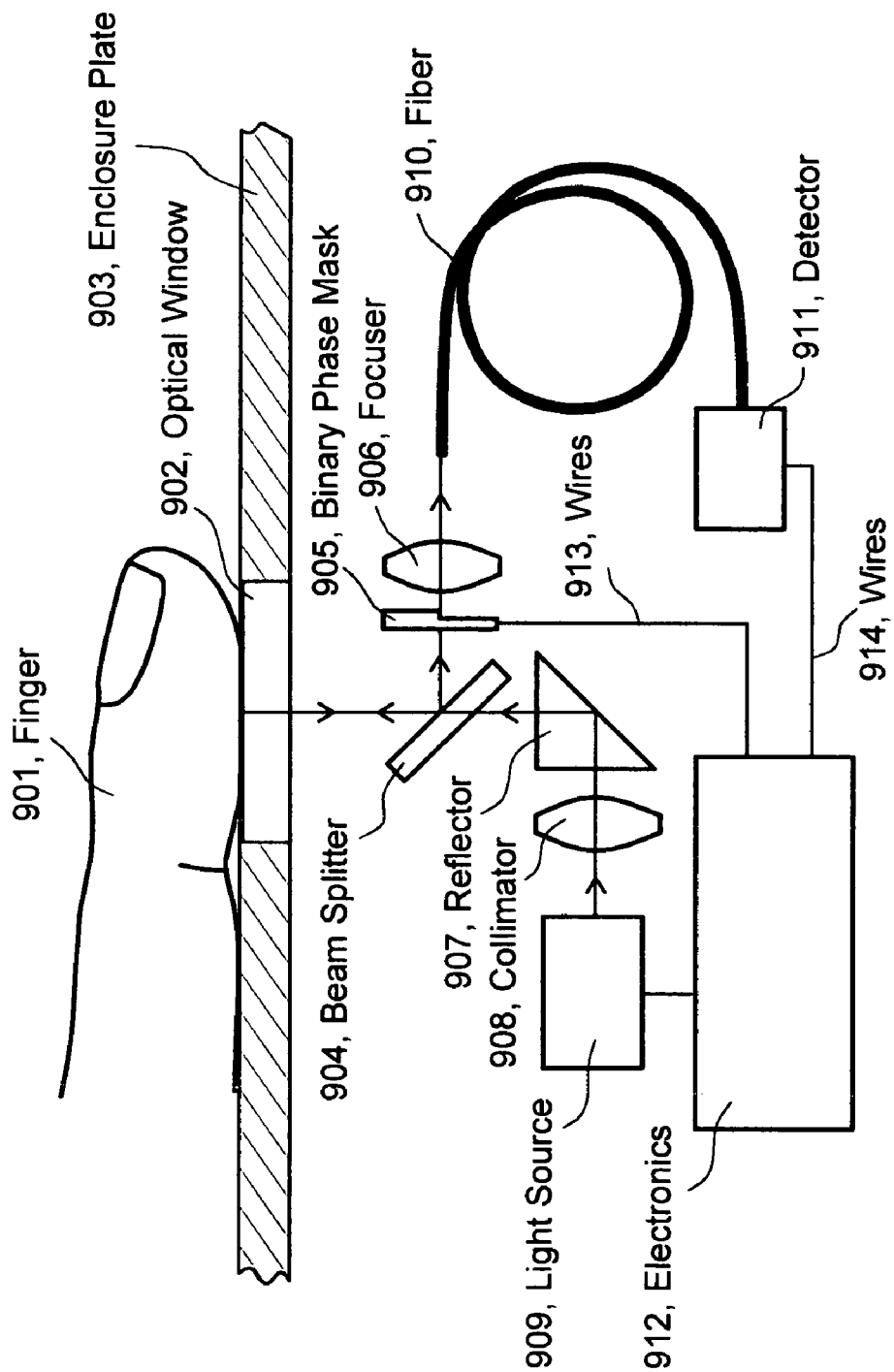
FIG. 9 shows an arrangement of an instrument for optically measuring substances beneath the skin of a finger tip.

Apparatus using the above described binary phase masking technique can be built for measuring human blood components non-invasively. An exemplary configuration for such a system is shown in FIG. 9. For measuring a blood component, such as glucose, a finger lays on top of the optical window. The interrogating light beam impinges on the skin though the window; the light reflected by the tissue is directed to pass a binary phase mask, 905, before being collected by the single-mode fiber. Either a dynamic or a stationary phase mask can be used. When a dynamic phase mask is used an electric signal is sent to the phase mask to control its phase retardation. When a wavelength tunable light source is utilized, the phase mask can be adjusted to follow the half wave condition, i.e. a π phase shift.

Figure 10:
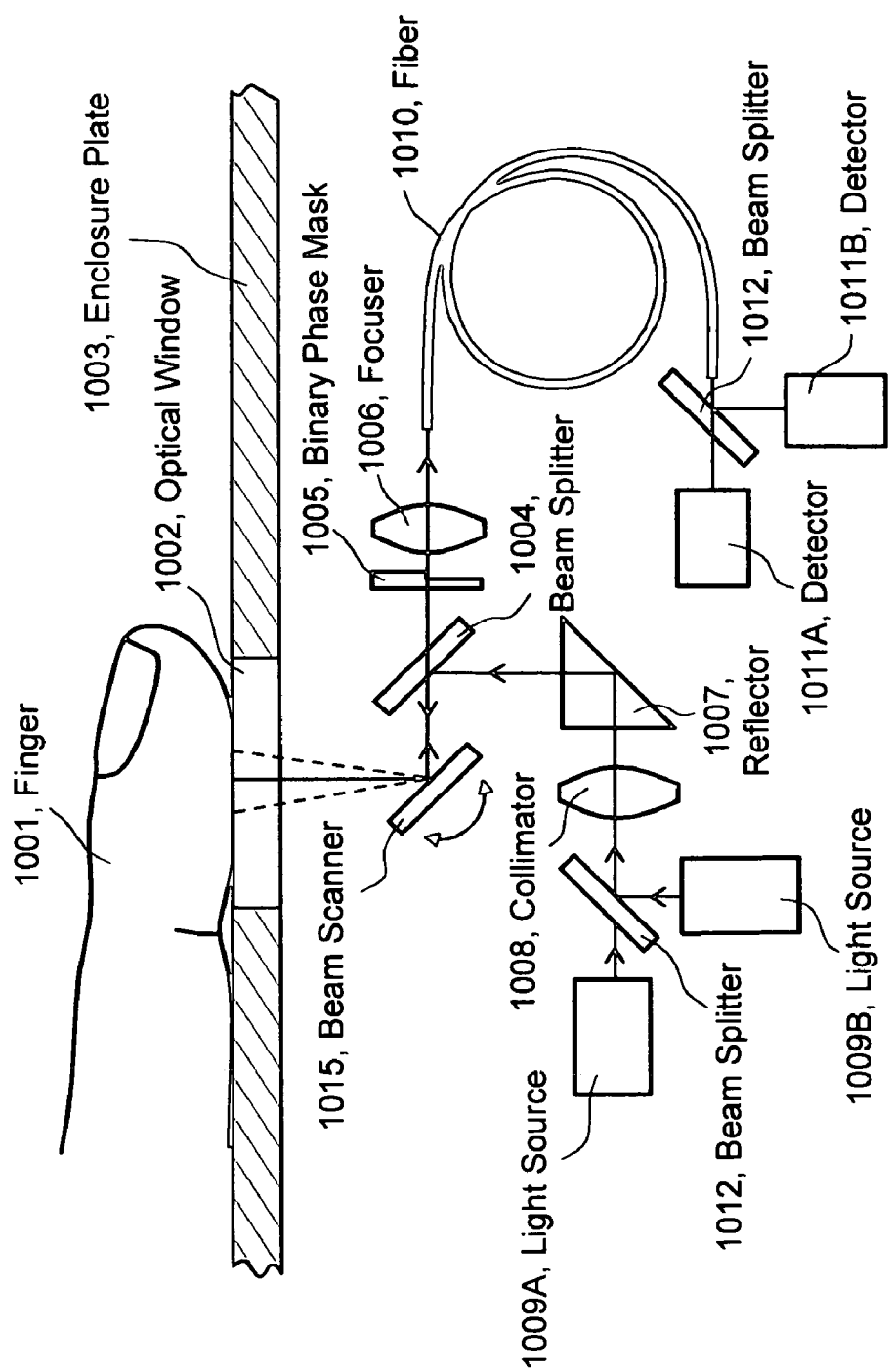
FIG. 10 shows an arrangement of an instrument for optically measuring substances beneath the skin of a finger tip; an optical beam scanner is employed.

To improve the reliability of the measurement the interrogating light beam can be made to steer, as shown in FIG. 10. The steering can reduce the variation caused by light hitting different anatomy of the skin so that an average and less variant optical signal can be produced. Either mechanical or non-mechanical beam steering system can be use for the purpose. One kind of simple of mechanical beam steering device is a rotating polygon. The configuration shown in FIG. 10 also includes the use of two light sources and two detectors.

Figure 11:
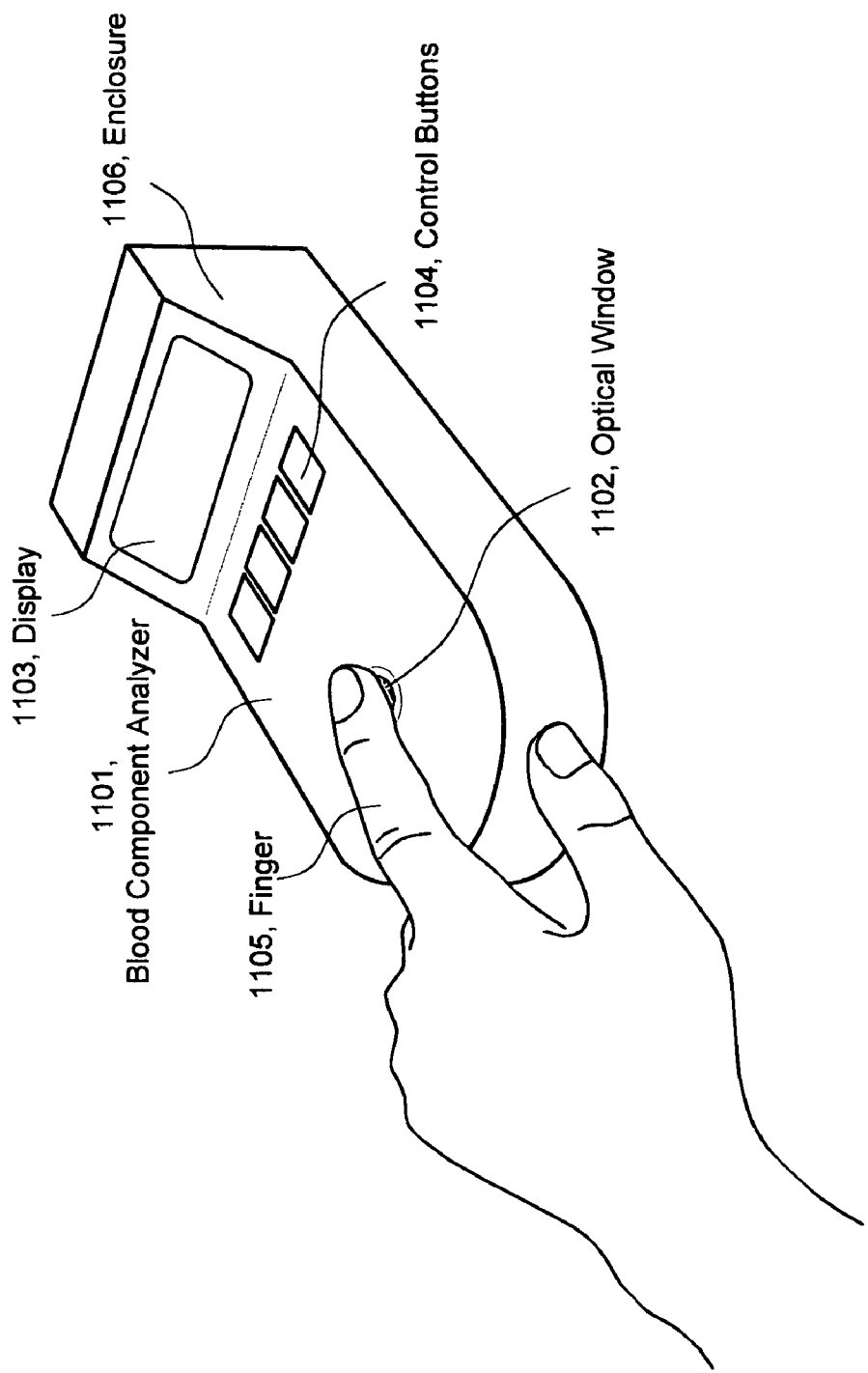
FIG. 11 shows the design of an instrument for non-invasively measuring blood substances of humans.

Miniaturized blood component analyzers can be build based on the above-described optical technique. Shown in FIG. 11 is a design for such a system. A finger or other body parts can be made to contact the optical window as the sampling point.

Figure 12:
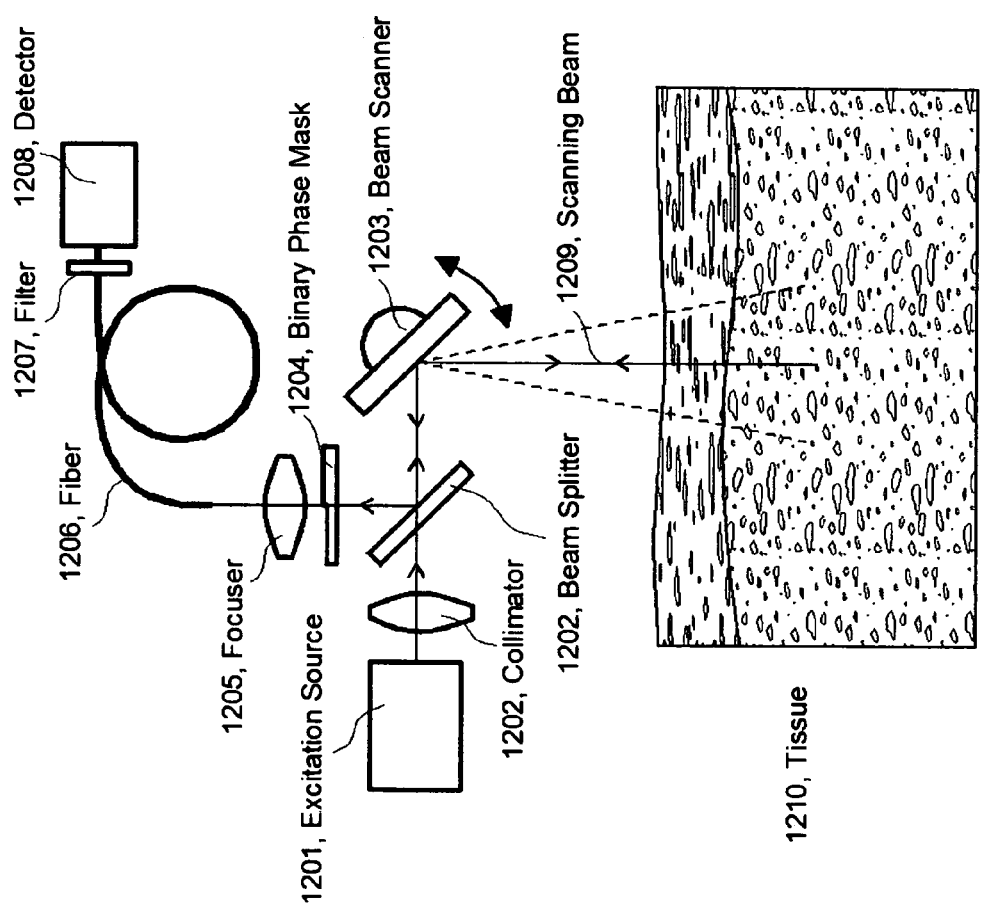
FIG. 12 shows an arrangement for measuring fluorescent light from a tissue with the use of a binary phase mask.

The binary phase masking technique can also be used to construct fluorescence-based tissue analyzer. Shown in FIG. 12 is one exemplary configuration. The light from the excitation source 1201 is directed, through a beam scanner, 1203, which provides either one-dimensional or two dimensional scanning, towards the tissue of interest. The part of the fluorescent light, propagating in the opposite direction, is made to pass a binary phase mask, 1204, before being collected by the single-mode fiber. An optical bandpass filter, 1207, can be used to select the fluorescent light for the detector.

Figure 13:
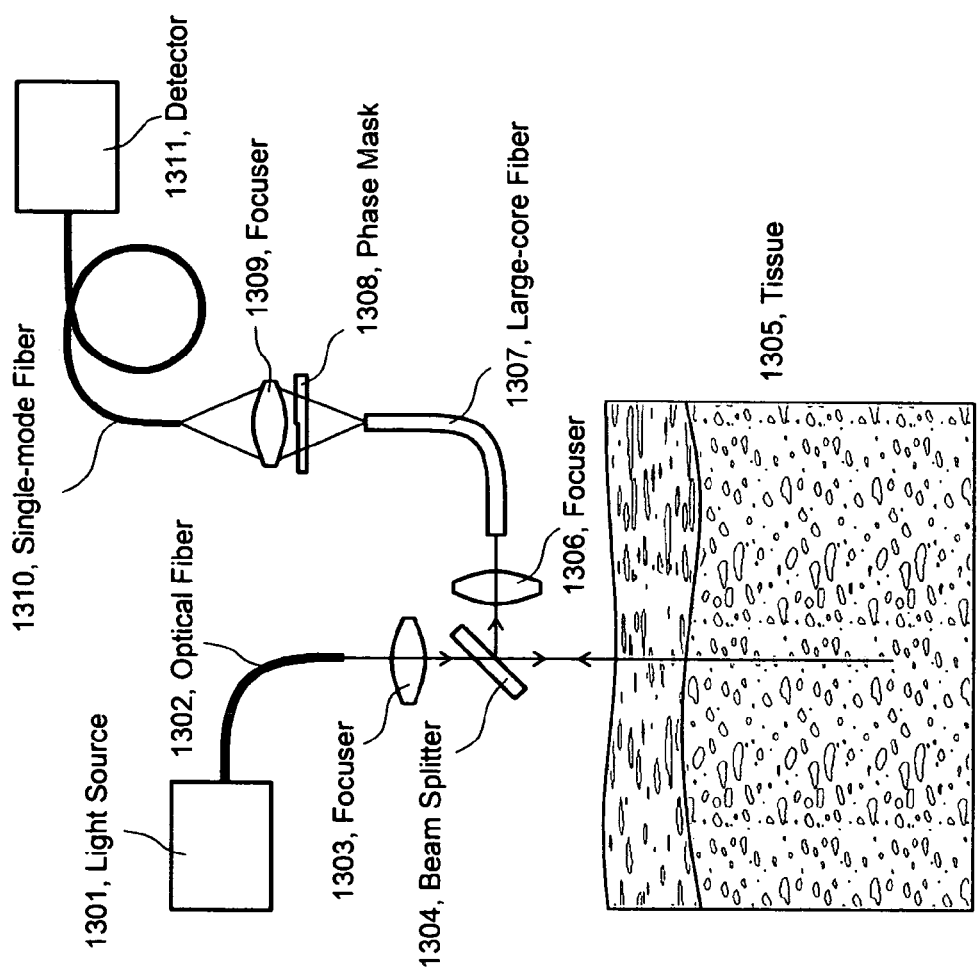
FIG. 13 shows an optical arrangement in which the backscattered light is first collected and transported through a large-core optical fiber to a position away from the tissue before a phase mask and a single-mode fiber are applied.

In another embodiment of the invented, the binary phase masks can be located away from the tissue through the use of a large-core optical fiber as shown in FIG. 13. In this arrangement the large-core fiber, 1307, serves to transport optical energy in undistorted and distorted wavefronts all to the binary phase mask, 1308, that is optically coupled to the other termination of the large-core fiber. The expanded light beam transmits through the binary phase mask before a focuser condenses the light onto a single-mode fiber, 1310. The binary phase mask suppresses the collection, by the single-mode fiber, of light carried by smooth wavefronts in the same fashion as previously described. Fiber 1307 should have sufficiently core size so that randomized wavefronts can be transported from one end to the other. In other words, the large-core fiber should support a sufficiently large number of propagation modes. The length of the large-core fiber should be short enough to avoid substantial mode coupling from happening inside the fiber.

What described above apply to electromagnetic waves of various wavelengths, from ultraviolet to infrared and beyond, including microwaves and radio-frequency waves. For analysis of biological tissues near-infrared and mid-infrared light can both be utilized. There are various kinds of light sources commercially available for the near-infrared range, including lasers, tunable lasers, superluminescent light emitting devices (SLED), fiber broadened light sources and incandescent sources; for mid-infrared range there are thermal sources and mid-infrared lasers and mid-infrared tunable lasers. Many types of photo detectors can be used in the tissue analyzing systems. They include, but limited to, semiconductor detectors, photomultiplier tubes and MEMS-based mid-infrared detectors.

Single-mode optical fibers are commercially available for both the near-infrared and mid-infrared wavelength ranges. Glass-core single-mode fibers are commonly used for communication. Polarization-maintaining optical fibers, such as what is produced by Corning Inc., can also be used in place of the single-mode fiber, either the slow mode or the fast mode can be selected to perform the functionality described above. Mid-infrared optical fibers include both solid core, such as silver-halide and chalcogenide, and hollow types. Both types can be made to propagate a single mode at particular wavelengths.

Figure 14:
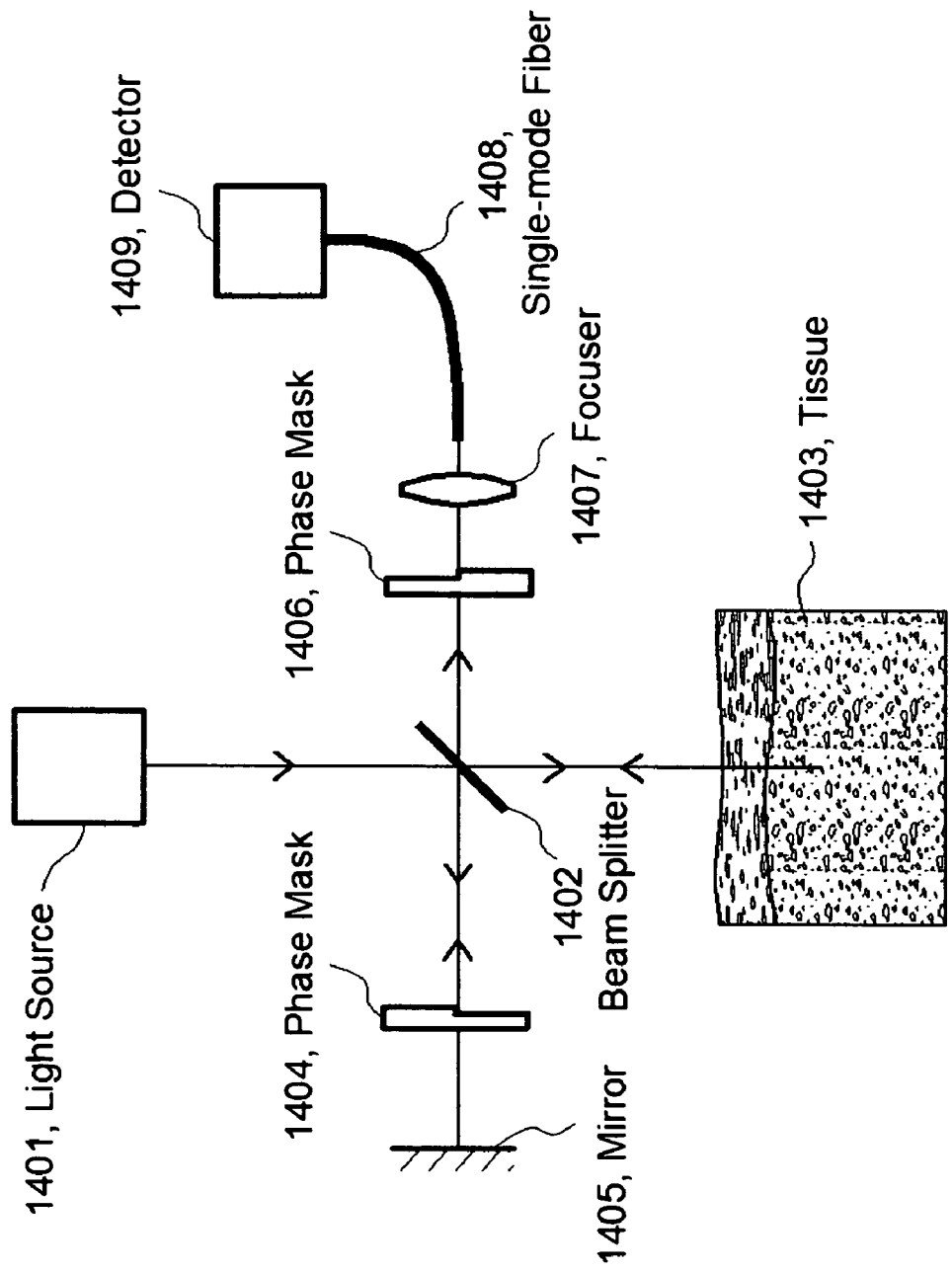
FIG. 14 shows an optical coherence tomography system in which binary phase masks are used to suppress specular reflection of the tissue surface and shallow scattering.

The use of binary phase mask can improve the imaging capability of optical coherence tomography. The optical arrangement shown in FIG. 14 is typical for optical coherence tomography except for the presence of the two binary phase masks, 1404 and 1406. Because of 1406, the backscattered light that is carried by smooth wavefronts will be preferentially rejected by the single-mode fiber, 1408. As a result, the specular reflection of the tissue surface can be substantially reduced from the acquired image. An additional advantage is the gain of the usable dynamic range of the detector, 1409. The use of the additional binary phase mask, 1404, is to cancel out the wavefront aberration in the reference light beam With this arrangement, due to the suppression of the high-intensity signal from the surface reflection and backscattering from shallow depth greater imaging depth can be achieved. It should be appreciated binary phase masks can be used in various optical arrangements for optical coherence tomography including free space or optical fiber based imaging systems.

Figure 15:
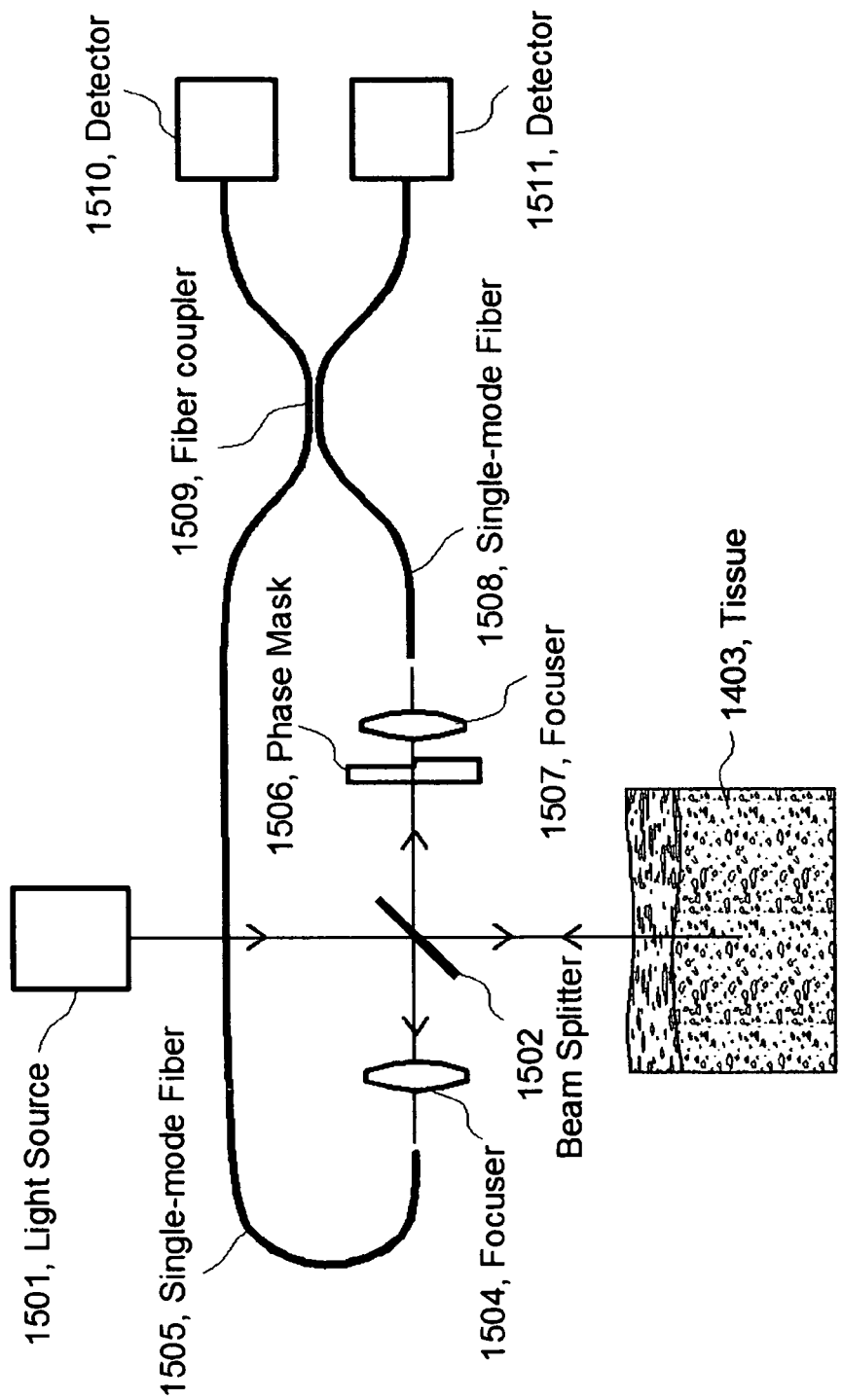
FIG. 15 shows an optical coherence tomography system in which a binary phase mask is employed in the collection optics to suppress collection of backscattered light of certain wavefront characteristics and to suppress the appearance of speckles.

FIG. 15 shows the use of a binary phase mask in an optical coherence tomography system in which fiber-optic components are utilized. With this arrangement, the use of the binary phase mask, 1508, will provide the same advantage as the system shown in FIG. 14. In addition, if a dynamic binary phase mask is used, a number of cross-sectional tissue images can be acquired under various phase patterns at the same tissue cross-sections. Averaging these images will produce a new image that contains less speckles. This is because the appearance of speckles is a consequence of collecting, by the single-mode fiber, backscattered light that possesses random wavefront aberration; exerting mathematically orthogonal binary phase masks, such as those shown in FIG. 2, will form tissue images of the same structural features but different speckle patterns. Averaging these images will produce a new image in which the speckles are smoothed out.

I claim what is disclosed in the description and in the drawings, including:

1. A device for optically characterizing living tissues, comprising:
    a light source that delivers a light beam to the tissue;
    an aberration means for exerting at least one spatial distribution of binary phase aberration to the light backscattered by the tissue;
    a focusing means;
    a single-mode optical fiber having one termination positioned to receive the light converged by said focusing means and the other termination optically coupled to a light-sensing component.

2. The device of claim 1, wherein:
    said aberration means is a composite aperture composed of a first group of segments having a first optical path length and a second group of segments having a second optical path length different from said first optical path length.

3. The device of claim 1, wherein:
    said aberration means is an aperture composed of two groups of angular sections of equal total angle span and different optical path length by one half of the center wavelength of the light source.

4. The device of claim 1, wherein:
    said aberration means has binary phase patterns that are changeable via a mechanical or a non-mechanical, including electro-optic, magneto-optic and thermal optic, means.

5. The device of claim 1, wherein:
    said aberration means has binary phase values that are tunable via a mechanical or a non-mechanical means including electro-optic effects.

6. A device for optically characterizing living tissues, comprising:
    a light source;
    a means for conveying a light beam from the source to the tissue;
    a binary phase mask placed in the path of the backscattered light from the tissue;
    a focusing means for converging the backscattered light;

a single-mode optical fiber positioned to collect the focused light from said focusing means with one termination; and a light-sensing component that is optically coupled to the other termination of the single-mode fiber.

7. The device of claim 6, wherein:

said phase mask is an aperture composed of two groups of angular sections of equal total angle span but different optical path length by one half of the center wavelength of the light source.

8. The device of claim 6, wherein:

said phase mask is composed of four quadrants having two opposite quadrants different from the remaining quadrants in optical path length by one half of the center wavelength of the light.

9. The device of claim 6, wherein:

said light source is a broadband source and said light sensing component is a spectrometer.

10. A device for optically characterizing living tissues, comprising:

a plurality of light sources;

a means for conveying a light beam from each of the sources to the same tissue site;

at least one binary phase mask placed in the path of the backscattered light from the tissue;

at least one focusing means for converging light energy;

at least one single-mode optical fiber positioned to collect the focused light from said focusing means with one termination; and a plurality of light-sensing components optically coupled to light radiations in different wavelength bands exiting the other termination of said single-mode optical fiber.

11. A device for optically characterizing living tissues, comprising:

a light source;

a beam steering means to cause the light to impinge on the tissue in a line or in an area;

a binary phase mask placed in the path of backscattered light from the tissue:

a focusing means for converging the backscattered light;

a single-mode optical fiber positioned to collect the focused light from said focusing means with one termination; and a light-sensing component that is optically coupled to the other termination of the single-mode fiber.

12. The device of claim 11, wherein:

said light source is a tunable laser and said binary phase mask can change its relative optical phase through a control signal.

13. The device of claim 11, wherein:

said binary phase mask is a reflection-mode device with a micro-electro-mechanical system (MEMS) having as least one stationary surface and one movable surface.

14. The device of claim 13, wherein:

said stationary and movable surfaces are shaped in strips.

15. A device for optically characterizing blood components, comprising:

a light source;

a beam steering means to cause the light to impinge on the skin of a finger in a line or in an area;

a binary phase mask placed in the path of the backscattered light from the tissue;

a focusing means for converging the backscattered light;

a single-mode optical fiber positioned to collect the focused light from said focusing means with one termination; and a light-sensing component that is optically coupled to the other termination of the single-mode fiber.

16. A device for optically characterizing living tissues, comprising:

a light source that emits a first wavelength;

a beam steering means to cause the light to impinge on the tissue in a line or in an area;

a binary phase mask placed in the path of fluorescent light emitted by the tissue at a second wavelength different from said first wavelength;

a focusing means for converging the fluorescent light;

a single-mode optical fiber positioned to collect the fluorescent light from said focusing means with one termination; and a light-sensing component that is optically coupled to the other termination of the single-mode fiber.

17. A device for optically characterizing living tissues, comprising:

a light source;

a light conduit that receives the backscattered light with its first termination and transports the light to its second termination;

a binary phase mask placed in the path of the light exiting the second termination of the light conduit;

a focusing means for converging the light that passes said binary phase mask;

a single-mode optical fiber positioned to collect the focused light from said focusing means with one termination; and a light-sensing component that is optically coupled to the other termination of the single-mode fiber.

18. A device for optically characterizing living tissues, comprising:

a light source;

a light splitting means for directing a first light beam to impinge on the tissue to be examined and directing a second light beam to a different path that bypasses the tissue;

a binary phase mask placed in the path of the backscattered light from the tissue;

an optical fiber receiving said backscattered light that passes through said binary phase mask;

a means for combining at least part of the light that travels through said optical fiber and at least part of said second light beam to produce two final light beams;

two photodetectors to receive said two final light beams, respectively.

19. The device of claim 18, wherein:

said binary phase mask is a composite aperture composed of a first group of segments having a first optical path length and a second group of segments having a second optical path length different from said first optical path length.

* * * * *